United States Patent
Minrovic et al.

(10) Patent No.: US 12,233,165 B2
(45) Date of Patent: Feb. 25, 2025

(54) MICROSPHERE FORMULATIONS COMPRISING KETAMINE AND METHODS FOR MAKING AND USING THE SAME

(71) Applicant: Oakwood Laboratories, LLC, Oakwood Village, OH (US)

(72) Inventors: Rachel Minrovic, Chardon, OH (US); Kelsey Kaht, Cleveland, OH (US); Tracy Richey, Kent, OH (US)

(73) Assignee: Oakwood Laboratories, LLC, Oakwood Village, OH (US)

( * ) Notice: Subject to any disclaimer, the term of this patent is extended or adjusted under 35 U.S.C. 154(b) by 411 days.

(21) Appl. No.: 17/404,128

(22) Filed: Aug. 17, 2021

(65) Prior Publication Data

US 2022/0054420 A1     Feb. 24, 2022

Related U.S. Application Data

(60) Provisional application No. 63/149,911, filed on Feb. 16, 2021, provisional application No. 63/067,068, filed on Aug. 18, 2020.

(51) Int. Cl.
*A61K 9/16* (2006.01)
*A61K 31/135* (2006.01)

(52) U.S. Cl.
CPC .......... *A61K 9/1647* (2013.01); *A61K 9/1682* (2013.01); *A61K 31/135* (2013.01)

(58) Field of Classification Search
None
See application file for complete search history.

(56) References Cited

U.S. PATENT DOCUMENTS

| | | |
|---|---|---|
| 6,291,013 B1 | 9/2001 | Gibson et al. |
| 6,479,007 B1 | 11/2002 | Greenberg et al. |
| 10,973,780 B2 | 4/2021 | Becker et al. |
| 2005/0260272 A1 | 11/2005 | Figueiredo et al. |
| 2011/0027331 A1 | 2/2011 | Hobot |
| 2013/0236573 A1 | 9/2013 | Singh et al. |
| 2015/0250719 A1 | 9/2015 | Meyer |
| 2018/0326080 A1 | 11/2018 | Deng et al. |
| 2021/0361578 A1 | 11/2021 | Salem et al. |

FOREIGN PATENT DOCUMENTS

| | | |
|---|---|---|
| WO | 2001010414 A1 | 2/2001 |
| WO | 02089767 A1 | 11/2002 |
| WO | 2005107706 A2 | 11/2002 |
| WO | 2007082061 A2 | 7/2007 |
| WO | 2013119183 A1 | 8/2013 |
| WO | 2019054948 A1 | 3/2019 |
| WO | 2021108801 A2 | 6/2021 |
| WO | 2021121366 A1 | 6/2021 |

OTHER PUBLICATIONS

International Preliminary Report on Patentability issued in PCT/US2021/046200, mailing date Feb. 21, 2023.
International Search Report and Written Opinion issued in PCT/US2021/046200, mailing date Jan. 5, 2022.
International Search Report and Written Opinion issued in PCT/US23/60315, mailing date Jul. 13, 2023.
Han, et al. "Formulation of Bioderable Ketamine Microparticles as an Analgesic Adjuvant Treatment Produced by Supercritical Fluid Polymer Encapsulation". Pharmac. vol. 10, No. 264, Dec. 6, 2018 (Dec. 6, 2018)—entire document especially p. 3, 8, Table 1, 2 and Abstract.
Zhu et al., "Bioerodable Ketamine-Loaded Microparticles Fabricated Using Dissolvable Hydrogel Template Technology", Journal of Pharmaceutical Sciences, 108 (2019) 1220-1226.
Han et al., "Formulation of Bioerodible Ketamine Microparticles as an Analgesic Adjuvant Treatment Produced by Supercritical Fluid Polymer Encapsulation", Pharmaceutics 2018, 10, 264.
Hirano et al, "Ketamine nano-delivery based on poly-lactic-co-glycolic acid (PLGA) nanoparticles", Applied Nanoscienc, vol. 8, Apr. 11, 2018.
Han, et al., "Novel Polymeric Bioerodable Microparticles for Prolonged-Release Intrathecal Delivery of Analgesic Agents for Relief of Intractable Cancer-Related Pain", Journal of Pharmaceutical Sciences 104:2334-2344, 2015.
International Preliminary Report on Patentability issued in PCT/US23/60315, dated Jun. 20, 2024 (9 pages).
China National Intellectual Property Administration, First Office Action issued in Chinese Patent Application No. 202180050934.4, dated Nov. 9, 2024 (3 pages).
Extended European search report issued on Sep. 26, 2024 in EP21858931.5.

*Primary Examiner* — Tigabu Kassa
(74) *Attorney, Agent, or Firm* — Benesch Friedlander Coplan & Aronoff

(57) ABSTRACT

Extended-release, injectable microsphere formulations comprising ketamine are provided. Methods for making and using the microsphere formulations are also provided.

6 Claims, 11 Drawing Sheets

MICROSPHERE FORMULATIONS COMPRISING KETAMINE AND METHODS FOR MAKING AND USING THE SAME

CROSS-REFERENCE TO RELATED APPLICATIONS

This application claims priority from U.S. Provisional Patent Application No. 63/067,068, filed on Aug. 18, 2020, and U.S. Provisional Patent Application No. 63/149,911, filed on Feb. 16, 2021, each of which is incorporated by reference herein in its entirety.

BACKGROUND

Ketamine (chemical formula $C_{13}H_{16}ClNO$, IUPAC name 2-(2-chlorophenyl)-2-(methylamino)cyclohexan-1-one), characterized by the general structure:

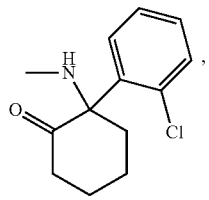 [SMILES: CNC1(c2ccccc2Cl)CCCCC1=O]

is an N-methyl-D-aspartate ("NMDA") receptor antagonist. Ketamine has primarily been used for anesthesia in humans and animals, as well as for chronic pain and sedation. Ketamine is typically available commercially in liquid form for use as an immediate-acting injection.

Ketamine is a racemic mixture of two enantiomers, (S)-(+)-ketamine and (R)-(−)-ketamine. The (S)-(+) enantiomer, also known as esketamine, is significantly more potent as an NMDA receptor antagonist and anesthetic than is the (R)-(−) enantiomer, also known as arketamine.

Ketamine and its enantiomers have also been investigated for treatment of depression. The U.S. Food and Drug Administration ("FDA") has approved esketamine for use, in conjunction with an oral antidepressant, for the treatment of treatment-resistant depression ("TRD") and major depressive disorder ("MDD") in adults. Specifically, the FDA approved Spravato® nasal spray. For the treatment of TRD, the manufacturer recommends that the drug be administered twice per week for the first four weeks, weekly for the next four weeks, then weekly or biweekly.

Ketamine is also used by recreational drug users and abusers. Ketamine is a Schedule III drug under the U.S. Drug Enforcement Agency's controlled substance classifications under the Controlled Substances Act. In part because of the significant possibility for diversion, Spravato® nasal spray is approved only for administration under the direct supervision of a healthcare provider. This requires a patient to make multiple trips per week to a doctor's office or hospital for the first four weeks, then weekly visits thereafter, making treatment inconvenient for the patient. Patients are also required to stay in the doctor's office or hospital for at least two hours after administration, adding to the patient's inconvenience. Until now, there has been a long felt yet unresolved need for a ketamine formulation that reduces the number of visits a patient needs to make to a provider's office to receive treatment, to reduce cost and inconvenience to the patient and the provider, while maintaining the ability to keep the drug in the hands of the healthcare providers to prevent diversion.

SUMMARY

Microsphere formulations comprising ketamine are provided. The microsphere formulations comprise polymer microspheres, each polymer microsphere comprising: (i) an active pharmaceutical ingredient ("API") comprising, consisting essentially of, or consisting of ketamine; and (ii) a biodegradable polymer comprising, consisting essentially of, or consisting of a poly(lactide) ("PLA") polymer. Each polymer microsphere may comprise a drug load of between about 10 wt/wt % to about 30 wt/wt %, and the polymer microspheres may have an average particle size of greater than 60 µm ($D_{50}$), including from about 80 µm ($D_{50}$) to about 110 µm ($D_{50}$). In some aspects, the polymer microspheres are characterized by a plurality of internal emulsions, each emulsion comprising water and a surfactant. In some aspects, the polymer microspheres may be subjected to dehydration, in which case the polymer microspheres are characterized by a plurality of internal macrovoids.

In some aspects, the polymer microspheres are double emulsified. A method for making double emulsified polymer microspheres is provided, the method comprising: (i) contacting ketamine with a biodegradable PLA polymer in the presence of a solvent to form an organic component and providing the organic component to a first homogenizer; (ii) providing an inner aqueous component comprising water and a first surfactant to the first homogenizer; (iii) homogenizing the organic component with the inner aqueous component to form a primary emulsion; (iv) providing the primary emulsion to a second homogenizer at a first flow rate; (v) providing a continuous phase comprising water and a second surfactant to the second homogenizer at a second flow rate; (vi) homogenizing the primary emulsion and the continuous phase; and (iv) removing the solvent to form the polymer microspheres, wherein each of the formed polymer microspheres incorporates at least a portion of the inner aqueous component in the form of a plurality of emulsions. In some aspects, the polymer microspheres may be subjected to dehydration, in which case the polymer microspheres are characterized by a plurality of internal macrovoids.

In another aspect, a method for treating depression, including TRD and/or MDD, is provided. The method may comprise administering to a patient in need thereof a microsphere formulation, the microsphere formulation comprising: polymer microspheres, each polymer microsphere comprising: (i) an API comprising, consisting essentially of, or consisting of ketamine; and (ii) a biodegradable polymer comprising, consisting essentially of, or consisting of a PLA polymer. Each polymer microsphere may comprise a drug load of between about 10 wt/wt % to about 30 wt/wt %, and the polymer microspheres may have an average particle size of greater than 60 µm ($D_{50}$), including from about 80 µm ($D_{50}$) to about 110 µm ($D_{50}$). In some aspects, the microsphere formulation is administered to the patient by intramuscular or subcutaneous injection with a dosing schedule of about every thirty days.

In another aspect, a method for treating pain is provided. The method may comprise administering by intramuscular or subcutaneous injection to a patient in need thereof a microsphere formulation made according to the methods described herein.

In another aspect, use is disclosed of a microsphere formulation comprising polymer microspheres, each polymer microsphere comprising: (i) an API comprising, consisting essentially of, or consisting of ketamine; and (ii) a biodegradable polymer comprising, consisting essentially of, or consisting of a PLA polymer, wherein each polymer microsphere may comprise a drug load of between about 10 wt/wt % to about 30 wt/wt %, and the polymer microspheres may have an average particle size of greater than 60 μm ($D_{50}$), including from about 80 μm ($D_{50}$) to about 110 μm ($D_{50}$), in the manufacture of a medicament for the treatment of depression.

In another aspect, a microsphere formulation comprising polymer microspheres, each polymer microsphere comprising: (i) an API comprising, consisting essentially of, or consisting of ketamine; and (ii) a biodegradable polymer comprising, consisting essentially of, or consisting of a PLA polymer, wherein each polymer microsphere may comprise a drug load of between about 10 wt/wt % to about 30 wt/wt %, and the polymer microspheres may have an average particle size of greater than 60 μm ($D_{50}$), including from about 80 μm ($D_{50}$) to about 110 μm ($D_{50}$), is provided for use as a medicament for the treatment of depression.

DETAILED DESCRIPTION

Figure 1:
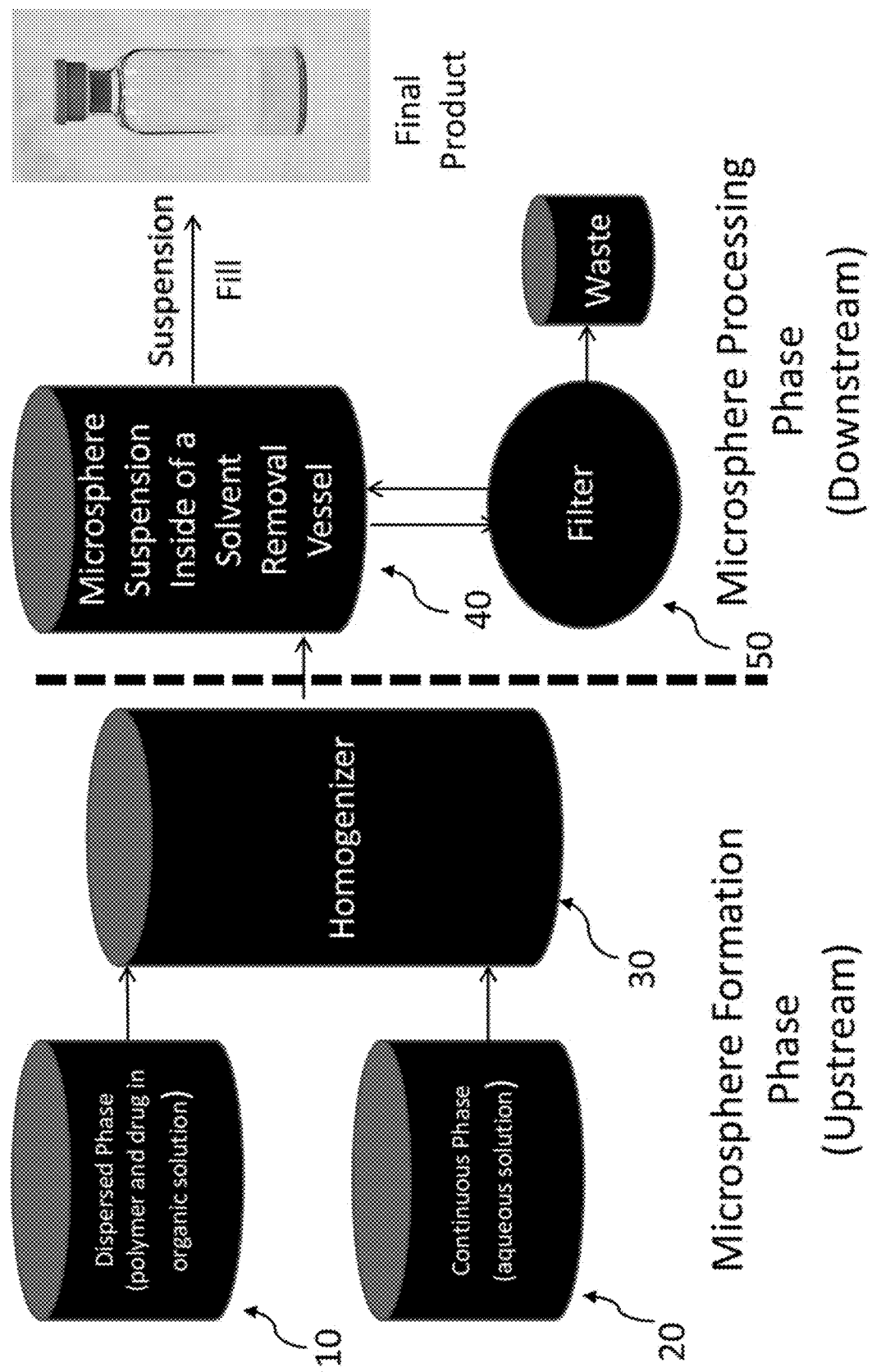
FIG. 1 is a flow chart illustrating an example method for making a single-emulsified microsphere formulation.

Microsphere formulations comprising ketamine are provided. The microsphere formulations comprise polymer microspheres, each polymer microsphere comprising: (i) an API comprising, consisting essentially of, or consisting of ketamine; and (ii) a biodegradable polymer comprising, consisting essentially of, or consisting of a PLA polymer. Each polymer microsphere may comprise a drug load of between about 10 wt/wt % to about 30 wt/wt %, and the polymer microspheres may have an average particle size of greater than 60 μm ($D_{50}$), including from about 80 μm ($D_{50}$) to about 110 μm ($D_{50}$). In some aspects, the polymer microspheres are characterized by a plurality of internal emulsions, each emulsion comprising water and a surfactant. In some aspects, the polymer microspheres may be subjected to dehydration, in which case the polymer microspheres are characterized by a plurality of internal macrovoids.

In some aspects, the polymer microspheres are double emulsified. A method for making double-emulsified polymer microspheres is provided, the method comprising: (i) contacting ketamine with a biodegradable PLA polymer in the presence of a solvent to form an organic component and providing the organic component to a first homogenizer; (ii) providing an inner aqueous component comprising water and a first surfactant to the first homogenizer; (iii) homogenizing the organic component with the inner aqueous component to form a primary emulsion; (iv) providing the primary emulsion to a second homogenizer at a first flow rate; (v) providing a continuous phase comprising water and a second surfactant to the second homogenizer at a second flow rate; (vi) homogenizing the primary emulsion and the continuous phase; and (iv) removing the solvent to form the polymer microspheres, wherein each of the formed polymer microspheres incorporates at least a portion of the inner aqueous component in the form of a plurality of emulsions. In some aspects, the polymer microspheres may be subjected to dehydration, in which case the polymer microspheres are characterized by a plurality of internal macrovoids.

API—Ketamine

In some aspects, the ketamine comprises a racemic mixture. In some aspects, the ketamine may comprise esketamine to the exclusion of arketamine. Alternatively, the ketamine may comprise arketamine to the exclusion of esketamine.

In some aspects, the ketamine may comprise a pharmaceutically acceptable salt form or a free base form of any of ketamine, esketamine to the exclusion of arketamine, and arketamine to the exclusion of esketamine. Suitable salts may include hydrochloride, sulfate, acetate, phosphate, diphosphate, chloride, maleate, citrate, mesylate, nitrate, tartrate, gluconate, and the like. In other aspects, a complex salt may be used to decrease solubility, such as ketamine palmitate, ketamine benzoic acid, ketamine tosylic acid, ketamine camphor-sulfonic acid, and the like.

Unless otherwise noted, as used herein, the term "ketamine" is intended to include the racemic mixture as well as both of its individual enantiomers. In some aspects, the ketamine may be used in its racemic form. Alternatively, the ketamine may be used in its enantiomeric forms, such as in its "S" or "R" forms. An aspect may also include purified forms of the enantiomeric forms. For example, and without limitation, the "S" enantiomer to "R" enantiomer ratio may be from 51:49 up to 100:0 and every range included therein. Alternative aspects may comprise more purified forms of the "R" enantiomer over the "S" enantiomer. For example, and without limitation, the "R" enantiomer to "S" enantiomer ratio may be from 51:49 up to 100:0, and every range included therein. Each enantiomer may also exist in its (+) or (−) forms, such as in S(+) or S(−) forms. An alternative aspect is the use of a purified form of esketamine in which the ratio of S(+) to S(−) may be from 51:49 up to 100:0, and every range included therein. An alternate aspect is the use of a purified form of esketamine in which the ratio of S(−) to S(+) may be from 51:49 up to 100:0, and every range included there.

In one aspect, the API consists or consists essentially of (S)-ketamine base (esketamine base). In one aspect, the microsphere formulation is exclusive of hydromorphone.

Biodegradable Polymers

PLA may be a suitable biodegradable polymer. In one aspect, the PLA may have an inherent viscosity ("IV") between about 0.30 to about 1.8 dL/g, including from about 0.60 to about 0.70 dL/g, and including about 0.66 dL/g or about 0.67 dL/g. In another aspect, the PLA may have an IV of about 0.67 dL/g. In one aspect, the biodegradable polymer is an Ashland DL 07E PLA polymer have an IV of about 0.67 dL/g.

As the phrase is used herein, a "poly(lactide) polymer" is to be distinguished from and does not include a poly(lactic-co-glycolic acid) polymer. When a poly(lactic-co-glycolic acid) is intended, it will be explicitly recited. In certain, explicitly recited aspects, suitable biodegradable polymers may include poly(lactic-co-glycolic acid) ("PLGA") copolymers, polyesteramides, polyanhydrides, polyacetals, polycaprolactones, and polycarbonates. In some aspects, the biodegradable polymer may comprise a PLGA copolymer having a co-monomer ratio for lactide to glycolide content of about 50:50 to about 85:15. In one aspect, the biodegradable polymer may have an average molecular weight from about 30 kDa to about 300 kDa.

In some aspects, copolymers are specifically excluded. In one aspect, PLGA polymers are specifically excluded. In some aspects, PLGA polymers having a co-monomer ratio for lactide to glycolide content of about 50:50 are specifically excluded.

In some aspects, the biodegradable polymers are ester end-capped. In some aspects, acid end-capped biodegradable polymers are specifically excluded.

Dispersed Phase/Organic Component—Solvents

The ketamine and the polymer may be dissolved in a solvent mixture to form a dispersed phase (when using a single emulsion technique) or an organic component (when using a double emulsion technique). Suitable solvents may include methylene chloride (also known as dichloromethane or DCM), ethanol, ethyl acetate, acetic acid, acetone, acetonitrile, acetyl acetone, acrolein, acrylonitrile, allyl alcohol, 1,3-butanediol, 1,4-butanediol, 1-butanol, 2-butanol, tert-butanol, 2-butoxyethanol, n-butyl amine, butyl dioxitol acetate, butyraldehyde, butyric acid, 2-chloroethanol, diacetone alcohol, diacetyl, diethylamine, diethylene glycol diethyl ether, diethylene glycol dimethyl ether, diethylene glycol monobutyl ether, diethylene glycol monobutyl ether acetate, diethylene glycol monoethyl ether, diethylene glycol monoethyl ether acetate, diethylene glycol monomethyl ether, N,N-diethylnicotinamide, dimethyl sulfoxide, N,N-dimethylacetamide, N,N-dimethylformamide, 1,4-dioxane, 2-ethoxyethanol, 2-ethoxyethyl acetate, ethyl acetate, ethyl formate, ethylene glycol methyl ether acetate, formic acid, furfural, glycofurol, hexylene glycol, isobutanol, isopropyl alcohol, 2,6-lutidine, methyl acetate, methyl ethyl ketone, methyl isopropyl ketone, methyl propionate, N-methylpyrrolidone, morpholine, tert-pentanol, 2-picoline, 3-picoline, 4-picoline, piperidine, 1-propanol, propionaldehyde, propylene oxide, pyridine, pyrimidine, pyrrolidine, tetrahydrofuran, tetramethylurea, triacetin, triethylene glycol, trimethyl phosphate, and combinations thereof. In some aspects, the solvent comprises DCM, ethanol, ethyl acetate, or a combination of two or all of them. In some aspects, the solvent consists or consists essentially of a combination of DCM and ethanol. In some aspects, the solvent consists or consists essentially of an about 5:1 (by volume) ratio of DCM:ethanol.

Double Emulsified Polymer Microspheres—Inner Aqueous Component

In one aspect, the organic component is homogenized with an inner aqueous component to form a primary emulsion. In one aspect, the inner aqueous component comprises water. In one aspect, the inner aqueous component comprises water and a surfactant. In one aspect, the surfactant comprises polyvinyl alcohol ("PVA"). In some aspects, the inner aqueous component comprises PVA in an amount of about 0.35% to about 1.0% by weight in water. In some aspects, the inner aqueous component comprises PVA in an amount of about 0.35% by weight in water. In some aspects, the inner aqueous component comprises PVA in an amount of about 1.0% by weight in water.

Figure 11A:
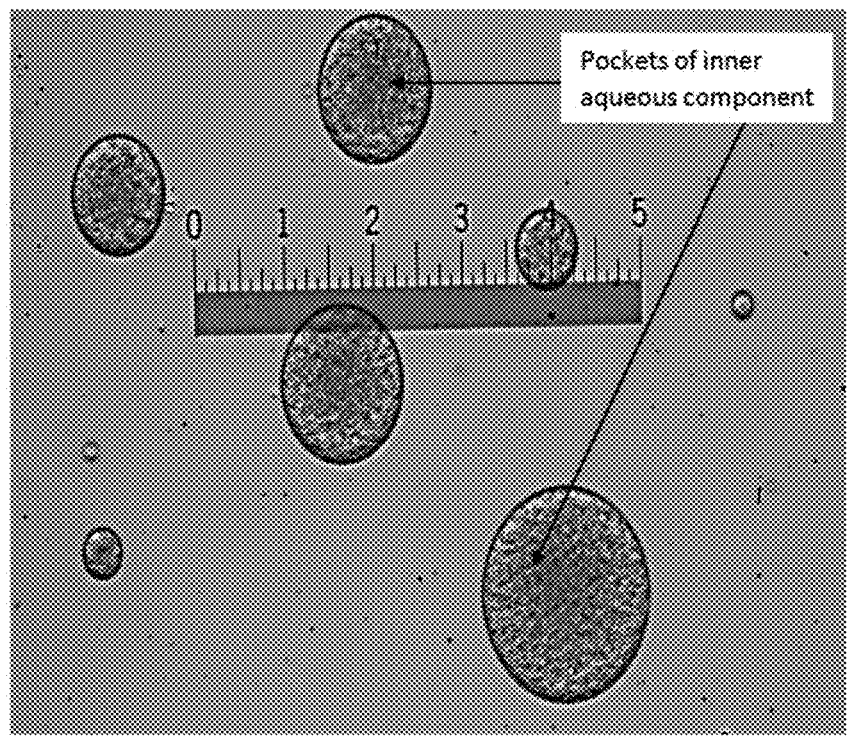
FIGS. 11A and 11B are two photographs showing a comparison between polymer microspheres prepared using a double emulsion technique (FIG. 11A) and a single emulsion technique (FIG. 11B), each prior to dehydration.
Figure 11B:
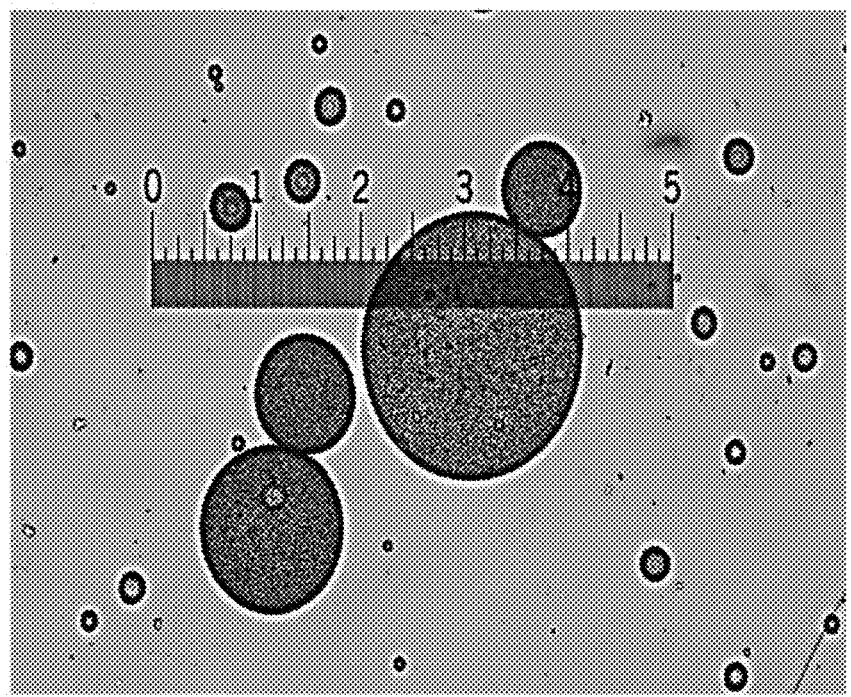

FIGS. 11A and 11B are two photographs showing a comparison between polymer microspheres prepared using a double emulsion technique (FIG. 11A) and a single emulsion technique (FIG. 11B), each prior to dehydration. The double emulsified polymer microspheres are characterized in that each of the polymer microspheres incorporates a plurality of emulsions comprising water and the surfactant. In some aspects, the polymer microspheres may be subjected to dehydration, in which case the polymer microspheres are characterized by a plurality of internal macrovoids.

In one aspect, dehydration may be achieved by freeze drying, including by lyophilization or cryodesiccation, i.e., a low temperature dehydration process that involves freezing the polymer microspheres, lowering pressure, and removing the ice by sublimation. This is in contrast to dehydration methods that evaporate water using heat.

Continuous Phase

The dispersed phase or the primary emulsion may be homogenized with a continuous phase comprising water and, optionally, a surfactant, such as PVA, to form a secondary emulsion. The surfactant component may be present in the continuous phase in an amount of about 0.35% to about 1.0% by weight in water. In one aspect, the surfactant component comprises PVA in an amount of about 0.35% by weight in water. In one aspect, the surfactant component comprises PVA in an amount of about 1.0% by weight in water. The secondary emulsion may be subjected to solvent removal and washing processes to form the double emulsified polymer microspheres.

In some aspects, the dispersed phase/primary emulsion flow rate to the homogenizer may from about 10 mL/min to about 30 mL/min, including about 20 mL/min and about 25 mL/min. In some aspects, the continuous phase flow rate to the homogenizer may be about 2 L/min. Thus, in one aspect, the continuous phase:dispersed phase/primary emulsion ratio may be from about 66:1 to about 200:1, including about 100:1 and about 80:1.

The continuous phase may be provided at room temperature or above or below room temperature. In some aspects, the continuous phase may be provided at about 40° C., about 37° C., about 35° C., about 30° C., about 25° C., about 20° C., about 15° C., about 10° C., about 5° C., about 0° C., and any range or value between any of those values.

Homogenizer

In some aspects, the homogenization of the organic component and the inner aqueous component may be conducted in a high-speed homogenizer, e.g., in a T25 Ultra-turrax high-speed homogenizer operating, e.g., at 21,500 rpm for 30 seconds to form the primary emulsion. In other aspects, the homogenization of the organic component and the inner aqueous component may be conducted in a sonicator, e.g., a Q700 Sonicator (manufactured by Qsonica), or in a magic LAB® DISPAX-REACTOR® DR (manufactured by IKA).

In some aspects, the homogenization of the dispersed phase/primary emulsion and the continuous phase may be conducted in an emulsifier or a homogenizer. For brevity, and because the methods are equally applicable to either, the phrase "homogenizer" contemplates a system or apparatus that can homogenize the dispersed phase/primary emulsion and the continuous phase, emulsify the dispersed phase/primary emulsion and the continuous phase, or both, which systems and apparatuses are known in the art. For example, in one aspect, the homogenizer is an in-line Silverson Homogenizer (commercially available from Silverson Machines, Waterside UK) or a Levitronix® BPS-i100 integrated pump system used, e.g., as described in US20210001290, which is incorporated by reference herein in its entirety. In one aspect, the homogenizer is a membrane emulsifier. In one aspect, the homogenizer runs at an impeller speed of about 1,000 to about 4,000 revolutions per minute ("RPM"), including about 1,600 RPM.

Average Particle Size

The polymer microspheres may be any size that is safely and efficaciously injectable by intramuscular or subcutaneous injection. In one aspect, the polymer microspheres may have an average particle size greater than 60 μm ($D_{50}$) to about 110 μm ($D_{50}$), including between about 80 μm ($D_{50}$) and about 110 μm ($D_{50}$). In one aspect, particle sizes of 60 μm or less are excluded. In one aspect, particle sizes of less than 80 μm ($D_{50}$) are excluded.

Drug Load

The drug load of each polymer microsphere in a drug to polymer ratio, expressed as a percentage, may range from between about 10 wt/wt % to about 50 wt/wt %, from between about 10 wt/wt % to about 30 wt/wt %, or from between about 10 wt/wt % to about 20 wt/wt %.

Extended Release

The microsphere formulations are characterized in that they have an in vitro (under physiologically relevant conditions) and an in vivo duration of ketamine release of about 30 days. In some aspects, the microsphere formulations are characterized in that the ketamine is released from the polymer microspheres at an average rate of about 2.5% to about 3.5% per day over a 30-day period.

Therapeutic Benefits

Possible conditions that may be treated using the microsphere formulations include depression, TRD, MDD, conditions involving excitotoxicity including neurodegenerative diseases and benzodiazepine withdrawal, pain, and other diseases or conditions that may be treated by the inhibition of action of the NMDA receptor.

In one aspect, depression, TRD, or MDD may be treated using the microsphere formulations, wherein the microsphere formulations are administered every about 30 days.

In another aspect, a method for treating depression, including TRD and/or MDD, is provided. The method may comprise administering to a patient in need thereof a microsphere formulation, the microsphere formulation comprising: polymer microspheres, each polymer microsphere comprising: (i) an API comprising, consisting essentially of, or consisting of ketamine; and (ii) a biodegradable polymer comprising, consisting essentially of, or consisting of a PLA polymer, wherein each polymer microsphere may comprise a drug load of between about 10 wt/wt % to about 30 wt/wt %, and the polymer microspheres may have an average particle size of greater than 60 μm ($D_{50}$), including from about 80 μm ($D_{50}$) to about 110 μm ($D_{50}$). In some aspects, the microsphere formulation is administered to the patient by intramuscular or subcutaneous injection with a dosing schedule of about every thirty days.

In another aspect, a method for treating pain is provided. The method may comprise administering by intramuscular or subcutaneous injection to a patient in need thereof a microsphere formulation made according to the methods described herein.

In another aspect, use is disclosed of a microsphere formulation comprising polymer microspheres, each polymer microsphere comprising: (i) an API comprising, consisting essentially of, or consisting of ketamine; and (ii) a biodegradable polymer comprising, consisting essentially of, or consisting of a PLA polymer, wherein each polymer microsphere may comprise a drug load of between about 10 wt/wt % to about 30 wt/wt %, and the polymer microspheres may have an average particle size of greater than 60 μm ($D_{50}$), including from about 80 μm ($D_{50}$) to about 110 μm ($D_{50}$), in the manufacture of a medicament for the treatment of depression.

In another aspect, a microsphere formulation comprising polymer microspheres, each polymer microsphere comprising: (i) an API comprising, consisting essentially of, or consisting of ketamine; and (ii) a biodegradable polymer comprising, consisting essentially of, or consisting of a PLA polymer, wherein each polymer microsphere may comprise a drug load of between about 10 wt/wt % to about 30 wt/wt %, and the polymer microspheres may have an average particle size of greater than 60 μm ($D_{50}$), including from about 80 μm ($D_{50}$) to about 110 μm ($D_{50}$), is provided for use as a medicament for the treatment of depression.

The microsphere formulations are extended-release, injectable formulations for administration via intramuscular or subcutaneous injection and not intrathecally. In some aspects, the intramuscularly or subcutaneously injectable formulation may further include sodium carboxymethylcellulose, tween 80, and mannitol.

EXAMPLES

Example 1—General Preparation of Polymer Microspheres Comprising Ketamine Via a Single Emulsion Method Microsphere Formation Phase. With reference to FIG. 1, a dispersed phase ("DP") 10 is formed by dissolving a polymer matrix (such as a PLA or PLGA polymer) in an organic solvent (such as DMC or ethyl acetate), followed by the addition of ketamine with mixing until completely dissolved. The DP 10 is filtered using a 0.2 µm sterilizing PTFE or PVDF membrane filter (such as EMFLON, commercially available from Pall or SartoriousAG) and pumped into a homogenizer 30, such as an in-line Silverson Homogenizer (commercially available from Silverson Machines, Waterside UK) or a Levitronix i100 (as described in US20210001290), at a defined flow rate. A continuous phase ("CP") 20 comprising water and, optionally, PVA is also pumped into the homogenizer 30 at a defined flow rate. The speed of the homogenizer 30 is generally fixed to achieve a desired polymer microsphere size distribution. A representative continuous "upstream" microsphere formation phase is described in U.S. Pat. No. 5,945,126, which is incorporated by reference herein in its entirety.

Microsphere Processing Phase. The formed or forming microspheres exit the homogenizer 30 and enter a solvent removal vessel ("SRV") 40. Water may be added to the SRV 40 during microsphere formation to minimize the solvent level in the aqueous medium. After the DP 10 has been exhausted, the CP and water flow rates are stopped, and the washing steps are initiated. Solvent removal is achieved using water washing and a hollow fiber filter (commercially available as HFF from GE Healthcare) 50. A representative "downstream" microsphere processing phase is described in U.S. Pat. No. 6,270,802, which is incorporated by reference herein in its entirety.

The washed microspheres are collected and freeze-dried overnight in a lyophilizer (Virtis) to remove any moisture. The resulting microspheres are a free-flowing off-white bulk powder.

Example 2—Preparation of PLGA-Based Single Emulsion Microsphere Formulation

Batch No. 1: The DP was formed by dissolving 1.25 g of ester end-capped PLGA Evonik LG 855S polymer (IV=3.0 dL/g) in 25.5 g DCM, followed by the addition of esketamine (3.75 g) with mixing until completely dissolved. The DP was filtered and pumped at 30 mL/minute into a Silverson L4RT in-line homogenizer operating at 2,000 rpm. A CP comprising water and 0.35% PVA was simultaneously pumped into the homogenizer at 2 L/min to form the single emulsion.

The formed or forming microspheres exited the homogenizer and entered the SRV. Deionized water was added to the SRV at 2 L/min. Solvent removal was achieved using water washing and a hollow fiber filter. The bulk suspension was collected via filtration and lyophilized to obtain a free-flowing powder with a yield of about 45%.

Batch No. 1 was tested in an in vitro assay mimicking physiological conditions and resulted in esketamine release over a period of approximately 45 days, which was beyond the desired 30 day release profile.

Example 3—Preparation of PLA-Based Single Emulsion Microsphere Formulation

Batch No. 2: The DP was formed by dissolving 1.25 g of ester end-capped PLA Evonik LG 209S polymer (IV=2.9 dL/g) in 25.5 g DCM, followed by the addition of esketamine (3.75 g) with mixing until completely dissolved. The DP was filtered and pumped at 30 mL/minute into a Silverson L4RT in-line homogenizer operating at 2,000 rpm. A CP comprising water and 0.35% PVA was simultaneously pumped into the homogenizer at 2 L/min to form the single emulsion.

The formed or forming microspheres exited the homogenizer and entered the SRV. Deionized water was added to the SRV at 2 L/min. Solvent removal was achieved using water washing and a hollow fiber filter. The bulk suspension was collected via filtration and lyophilized to obtain a free-flowing powder with a yield of about 36%.

Batch No. 2 was tested in an in vitro assay mimicking physiological conditions and resulted in esketamine release over a period of approximately 60 days, which was beyond the desired 30 day release profile.

Example 4—Effect of Drug Load on Ketamine Release in PLGA-Based Single Emulsion Microsphere Formulations Batch No. 3: The DP was formed by dissolving 4.5 g of an ester end-capped PLGA Evonik LG 855S polymer (an 85:15 PLGA with ester end-caps and an inherent viscosity of 3.0 dL/g) in 65.0 g DCM, followed by the addition of esketamine (0.5 g) with mixing until completely dissolved. The DP was filtered and pumped at 30 mL/minute into a Silverson L4RT in-line homogenizer operating at 1,000 rpm. A CP comprising water and 0.35% PVA was simultaneously pumped into the homogenizer at 2 L/min to form the single emulsion.

The formed or forming microspheres exited the homogenizer and entered the SRV. Deionized water was added to the SRV at 2 L/min. Solvent removal was achieved using water washing and a hollow fiber filter. The bulk suspension was collected via filtration and lyophilized to obtain a free-flowing powder with a yield of about 9%. The drug load was 8.0 wt/wt % (80% drug encapsulation efficiency based on a target drug load of 10 wt/wt %).

Batch No. 3 was tested in an in vitro assay mimicking physiological conditions and resulted in esketamine release over a period of >60 days, which was beyond the desired release profile of 30 days. See FIG. 2.

Batch No. 4: To test the effect of drug load on ketamine release in PLGA-based single emulsion microsphere formulations, another batch (Batch No. 4) was prepared with a 75 wt/wt % target drug load. Thus, the DP was formed by dissolving 2.5 g of the same 85:15 PLGA as was used in Batch No. 3 in 51.0 g DCM, followed by the addition of esketamine (7.5 g) with mixing until completely dissolved. The DP was filtered and pumped at 30 mL/minute into a Silverson L4RT in-line homogenizer operating at 1,500 rpm. A CP comprising water and 0.35% PVA was simultaneously pumped into the homogenizer at 2 L/min to form the single emulsion.

The formed or forming microspheres exited the homogenizer and entered the SRV. Deionized water was added to the SRV at 2 L/min. Solvent removal was achieved using water washing and a hollow fiber filter. The bulk suspension was collected via filtration and lyophilized to obtain a free-flowing powder with a yield of about 34%. The drug load was 48.2 wt/wt % (64% drug encapsulation efficiency based on a target drug load of 75 wt/wt %).

Figure 2:
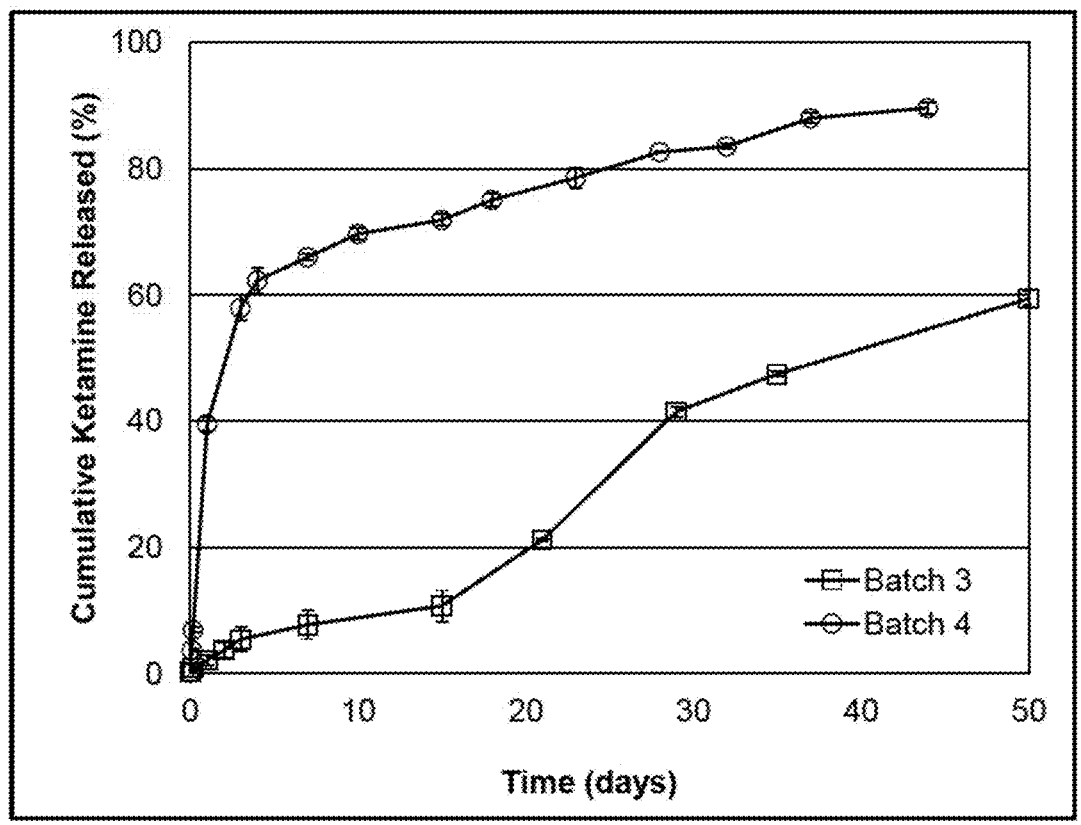
FIG. 2 is a graph showing an example effect of drug load on the amount of ketamine released in vitro over time from a microsphere formulation prepared using a single emulsification technique.

Batch No. 4 was tested in an in vitro assay mimicking physiological conditions. The cumulative percent release of ketamine over time is shown in FIG. 2. Batch No. 4 experienced an unacceptable substantial "burst," with >60% release in the first five days and continued to release ketamine beyond the desired 30 day release profile. See FIG. 2.

Example 5—Effect of Co-Monomer Ratio on Ketamine Release in PLGA- and PLA-Based Single Emulsion Microsphere Formulations Batch No. 5: To test the effect of co-monomer ratio, another batch (Batch No. 5) with a 75% drug load was prepared, this time using a PLA polymer. Thus, the DP was formed by dissolving 1.25 g of an ester end-capped Evonik LG 209S polymer (a PLA with IV=2.9 dL/g) in 26.0 g DCM, followed by the addition of esketamine (3.75 g) with mixing until completely dissolved. The DP was filtered and pumped at 30 mL/minute into a Silverson L4RT in-line homogenizer operating at 2,000 rpm. A CP comprising water and 0.35% PVA was simultaneously pumped into the homogenizer at 2 L/min to form the single emulsion.

The formed or forming microspheres exited the homogenizer and entered the SRV. Deionized water was added to the SRV at 2 L/min. Solvent removal was achieved using water washing and a hollow fiber filter. The bulk suspension was collected via filtration and lyophilized to obtain a free-flowing powder with a yield of about 46%. The drug load was 76.0 wt/wt % (101% drug encapsulation efficiency based on a target drug load of 75 wt/wt %). Polymer microspheres in Batch No. 5 had an average particle size of 52 μm ($D_{10}$), 108 μm ($D_{50}$), 184 μm ($D_{90}$).

Figure 3:
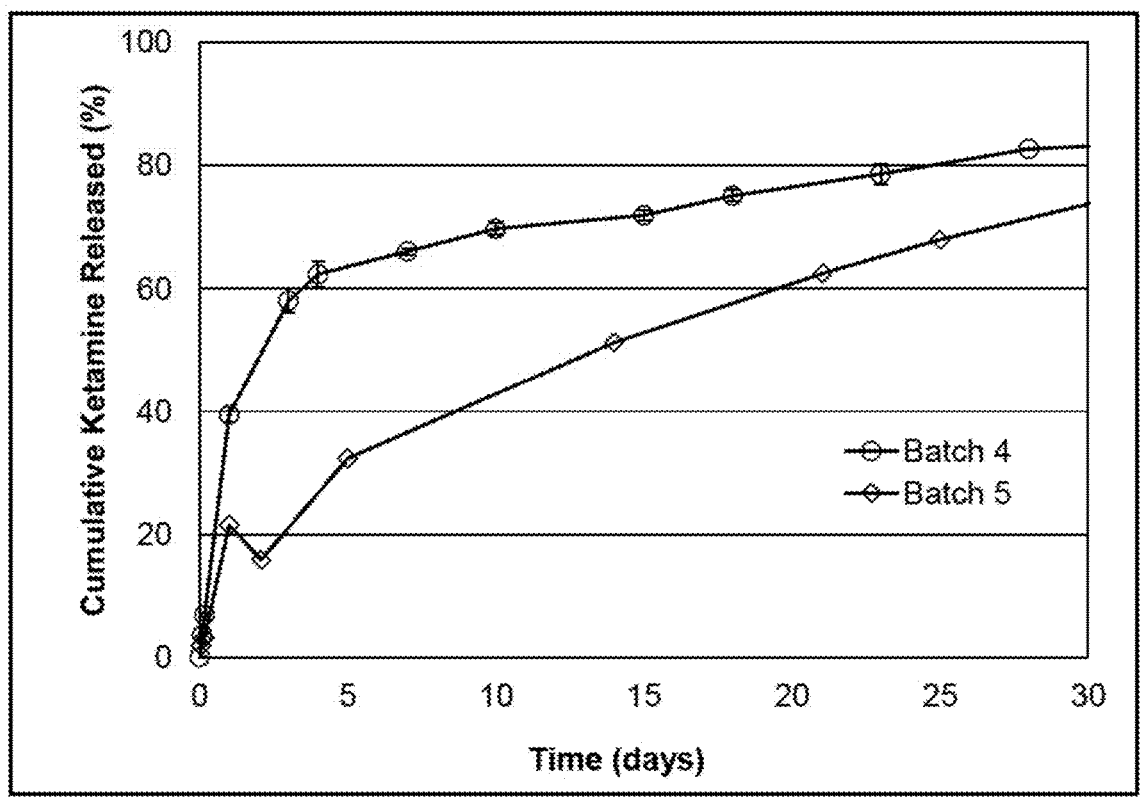
FIG. 3 is a graph showing an example effect of co-monomer ratio of the biodegradable polymer on the amount of ketamine released in vitro over time from a microsphere formulation prepared using a single emulsification technique.

Batch No. 5 was tested in an in vitro assay mimicking physiological conditions. The cumulative percent release of ketamine over time is shown in FIG. 3. Batch No. 5 experienced a much less substantial burst than Batch No. 4, with >30% release in the first five days. However, Batch No. 5 continued to release ketamine beyond the desired 30 day release profile.

Example 6—Effect of Polymer Microsphere Size on Ketamine Release in PLGA-Based Single Emulsion Microsphere Formulations Batch Nos. 6 and 6A: The DP for each batch was formed by dissolving 12.75 g of the same 85:15 PLGA polymer as used in Batch Nos. 3 and 4 in 255.0 g DCM, followed by the addition of esketamine (37.5 g) with mixing until completely dissolved. The DP was filtered and pumped at 30 mL/minute into a Silverson L4RT in-line homogenizer. For Batch No. 6, the homogenizer operated at 4,000 rpm. For Batch No. 6A, the homogenizer operated at 3,000 rpm. For each batch, a CP comprising water and 0.35% PVA was simultaneously pumped into the homogenizer at 2 L/min to form the single emulsion.

For each batch, the formed or forming microspheres exited the homogenizer and entered the SRV. Deionized water was added to the SRV at 2 L/min. Solvent removal was achieved using water washing and a hollow fiber filter. The bulk suspension was collected via filtration and lyophilized to obtain a free-flowing powder.

Batch No. 6 resulted in a yield of about 23%. The drug load was 17.0 wt/wt % (23% drug encapsulation efficiency based on a target drug load of 75 wt/wt %). The particle size was 8 μm ($D_{10}$), 27 μm ($D_{50}$), 57 μm ($D_{90}$).

Batch No. 6A resulted in a yield of about 29%. The drug load was 32.0 wt/wt % (43% drug encapsulation efficiency based on a target drug load of 75 wt/wt %). The particle size was 24 μm ($D_{10}$), 60 μm ($D_{50}$), 113 μm ($D_{90}$).

Figure 4:
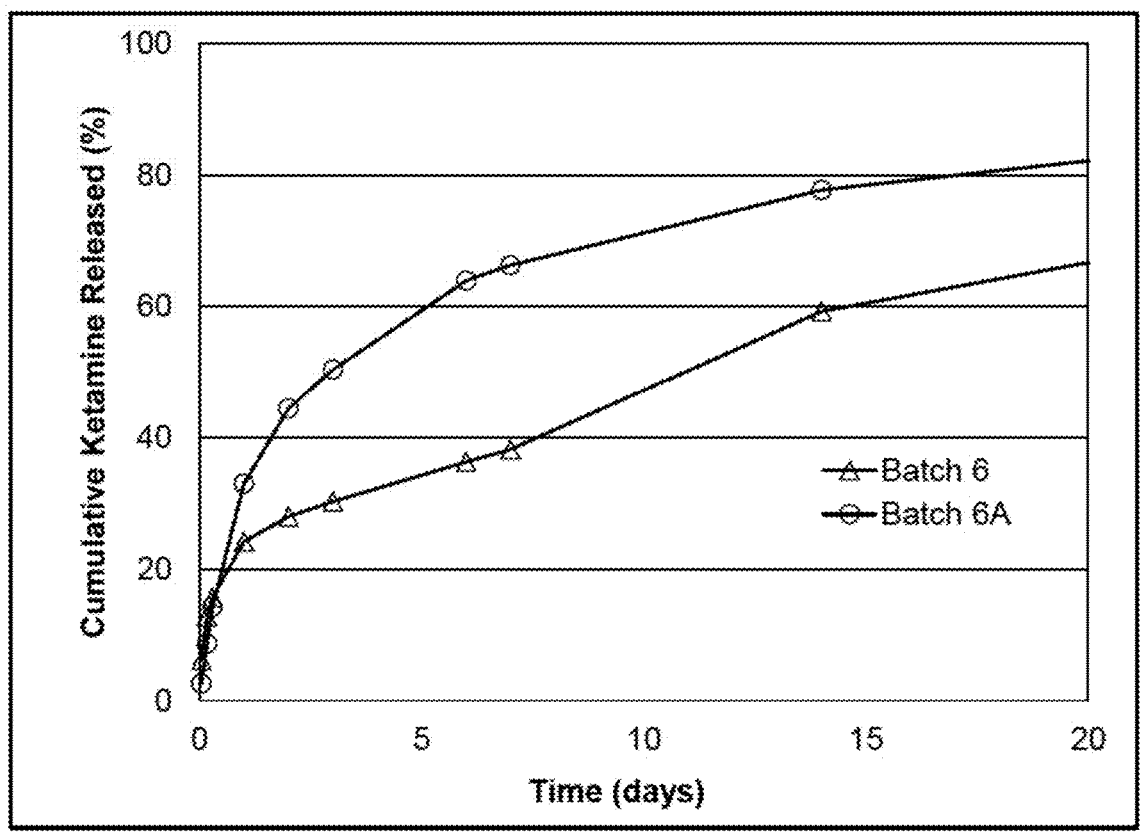
FIG. 4 is a graph showing the effect of average polymer microsphere size on the amount of ketamine released in vitro over time from a microsphere formulation prepared using a single emulsification technique.

Batch Nos. 6 and 6A were tested in an in vitro assay mimicking physiological conditions. The cumulative percent release of ketamine over time as a function of particle size is shown in FIG. 4. Batch Nos. 6 and 6A were ultimately deemed deficient because the yields and encapsulation efficiencies were insufficient.

Example 7—Effect of Ethyl Acetate as Solvent on Ketamine Release in PLA-Based Single Emulsion Microsphere Formulations Batch No. 7: The DP was formed by dissolving 7.0 g of an ester end-capped PLA Ashland Viatel 07 E polymer (IV=0.66 dL/g) in 31.5 g of ethyl acetate, followed by the addition of esketamine (3.0 g) with mixing until completely dissolved. The DP was filtered and pumped at 30 mL/minute into a Levitronix i100 (as described in US20210001290) operating at 1,600 rpm. A CP comprising water and 0.35% PVA was simultaneously pumped into the homogenizer at 2 L/min to form the single emulsion.

The formed or forming microspheres exited the homogenizer and entered the SRV. Deionized water was added to the SRV at 2 L/min. Solvent removal was achieved using water washing and a tangential flow filter. The bulk suspension was collected via filtration and lyophilized to obtain a free-flowing powder.

Batch No. 7 resulted in a yield of about 70%. The drug load was 25.6 wt/wt % (85% drug encapsulation efficiency based on a target drug load of 30 wt/wt %).

Figure 5:
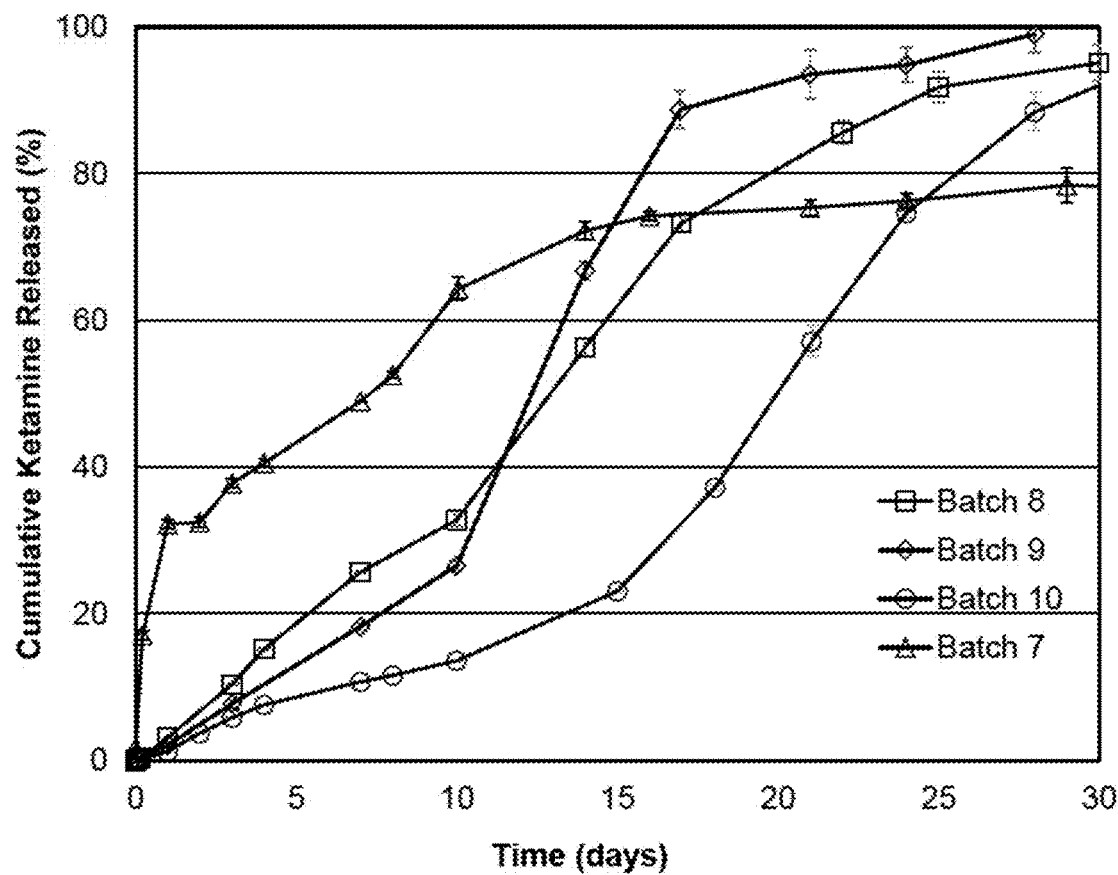
FIG. 5 is a graph showing an example effect of the inherent viscosity of the biodegradable polymer and/or choice of solvent on the release of ketamine in vitro over time from three example double emulsified microsphere formulations and one example single emulsified formulation.
Figure 8:
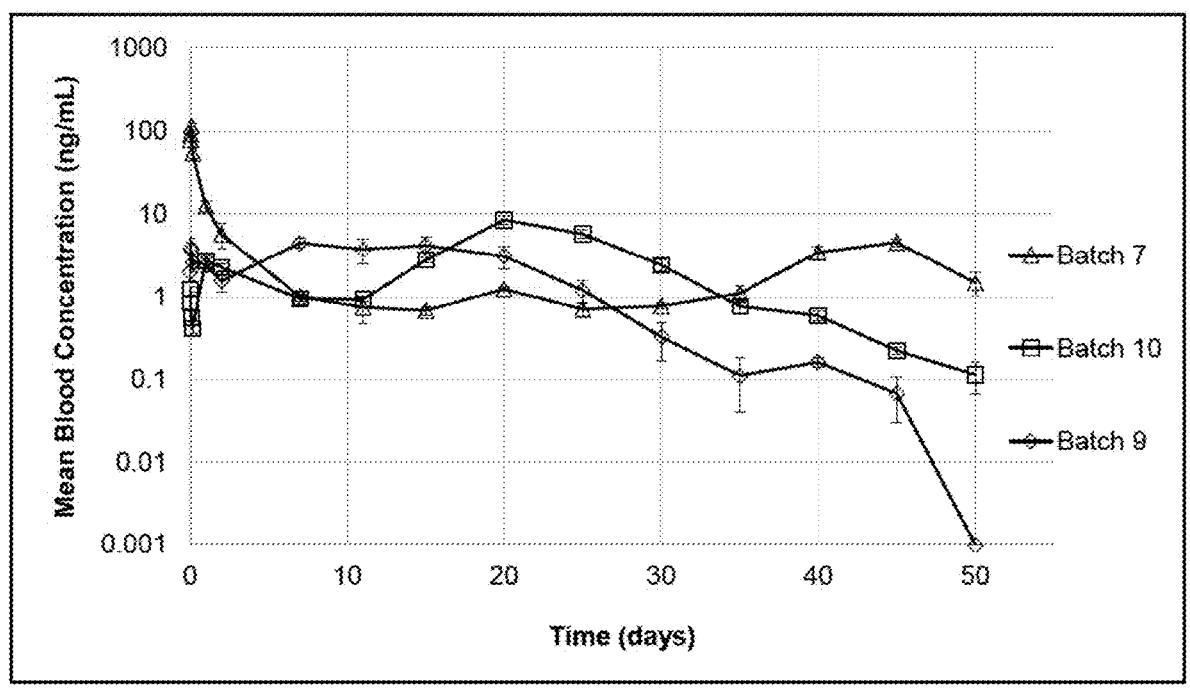
FIG. 8 is a graph showing example results of a pharmacokinetics study in rats using microsphere formulations as described herein.

Batch No. 7 was tested in an in vitro assay mimicking physiological conditions. The cumulative percent release of ketamine over time is shown in FIG. 5. Batch No. 7 was ultimately deemed deficient because of an unacceptably large burst (which is even more evident in vivo, as shown in FIG. 8).

Figure 6:
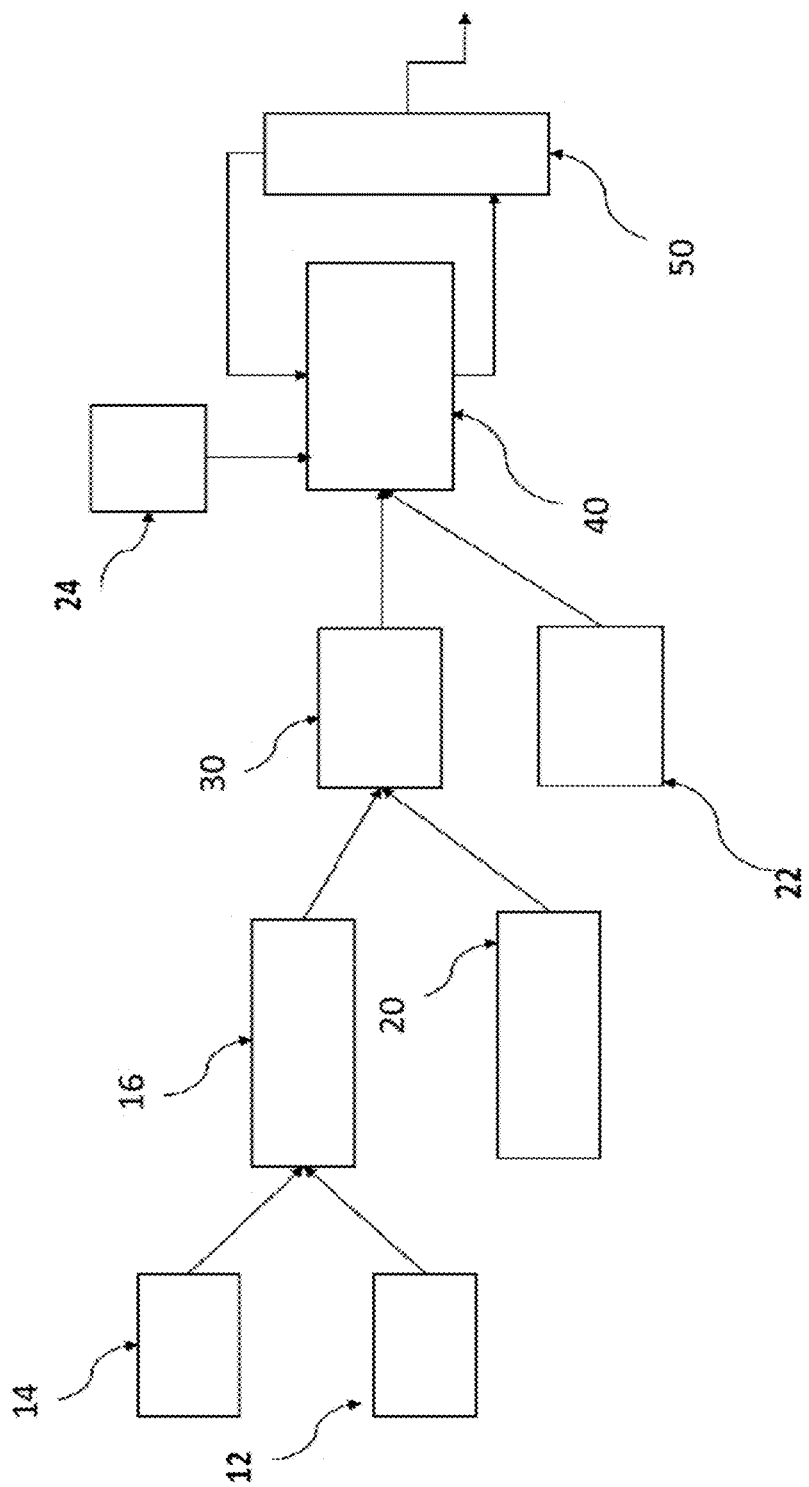
FIG. 6 is a flow chart illustrating an example method for making a double-emulsified microsphere formulation.

Example 8—General Preparation of Microsphere Formulations Comprising Ketamine Via a Double Emulsion Method Microsphere Formation Phase. Using like numerals for like elements to provide a juxtaposition to the single emulsion method depicted in FIG. 1, with reference to FIG. 6, an organic component 12 is formed by dissolving a biodegradable polymer (such as a PLA polymer) in an organic solvent (such as DCM, ethanol, or a combination thereof), followed by the addition of ketamine with mixing until completely dissolved. The organic component 12 is homogenized with an inner aqueous component ("IA component") 14 comprising water and, optionally, PVA, in a high-speed homogenizer probe (such as a T25 Ultra-turrax, sonicator, or magic Lab® DISPAX-REACTOR®) 16 to form a primary emulsion ("PE") in place of DP 10. The PE is pumped into a homogenizer 30, such as an in-line Silverson Homogenizer or a Levitronix i100 (as described in US20210001290), at a defined flow rate. The CP 20 comprising water and, optionally, PVA, is also pumped into the homogenizer 30 at a defined flow rate.

Microsphere Processing Phase. The formed or forming microspheres exit the homogenizer 30 and enter an SRV 40. Water 22 is added to the SRV 40 during microsphere formation to minimize the solvent level. The resulting suspension is mixed in the SRV 40 during the microsphere formation period. After the PE is exhausted, the CP and water flow additions are stopped, and the washing steps are initiated.

Solvent removal is achieved by washing the microspheres with ambient water 24 (i.e. 25° C.) and hot water (35-39° C.) and filtering them through a hollow fiber filter 50 (commercially available as HFF from GE Healthcare). Excess solvent is removed and discarded, and the filtered microspheres are returned to the SRV until the desired level of solvent is removed from the microsphere formulation.

The washed microspheres are collected on a filter membrane and freeze-dried overnight in a lyophilizer (Virtis) to remove moisture. The resulting microspheres are a free-flowing off-white bulk powder.

The double emulsification method consistently resulted in surprisingly high yields compared to the single emulsification method.

Example 9—Preparation and Evaluation of a Low Inherent Viscosity (0.66 dL/g) PLA-Based Double Emulsion Microsphere Formulation Batch No. 8: The organic component was formed by dissolving 7.0 g of an ester end-capped PLA Ashland Viatel 07 E polymer (IV=0.66 dL/g) in 39 g of DCM and 4.6 g of ethanol (5:1 ratio by volume), followed by the addition of esketamine (3.0 g) with mixing until completely dissolved. The organic component was homogenized with an IA component consisting of 1 mL of de-ionized water in a T25 Ultra-turrax high-speed homogenizer operating at 21,500 rpm for 30 seconds to form the PE.

The PE was pumped into a Levitronix i100 (as described in US20210001290) operating at 1,600 rpm at a rate of 30 mL/minute, along with a CP comprising water and 0.35% PVA, which was pumped at a rate of 2 L/min, for a CP:PE ratio of 66:1.

The formed or forming microspheres exited the homogenizer and entered an SRV. Deionized water was added to the SRV at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to obtain a free-flowing powder with a yield of about 59%. The drug load was 16.5 wt/wt % (55% drug encapsulation efficiency based on a target drug load of 30 wt/wt %). The average particle size was 47 μm ($D_{10}$), 82 μm ($D_{50}$), 132 μm ($D_{90}$).

Figure 7:
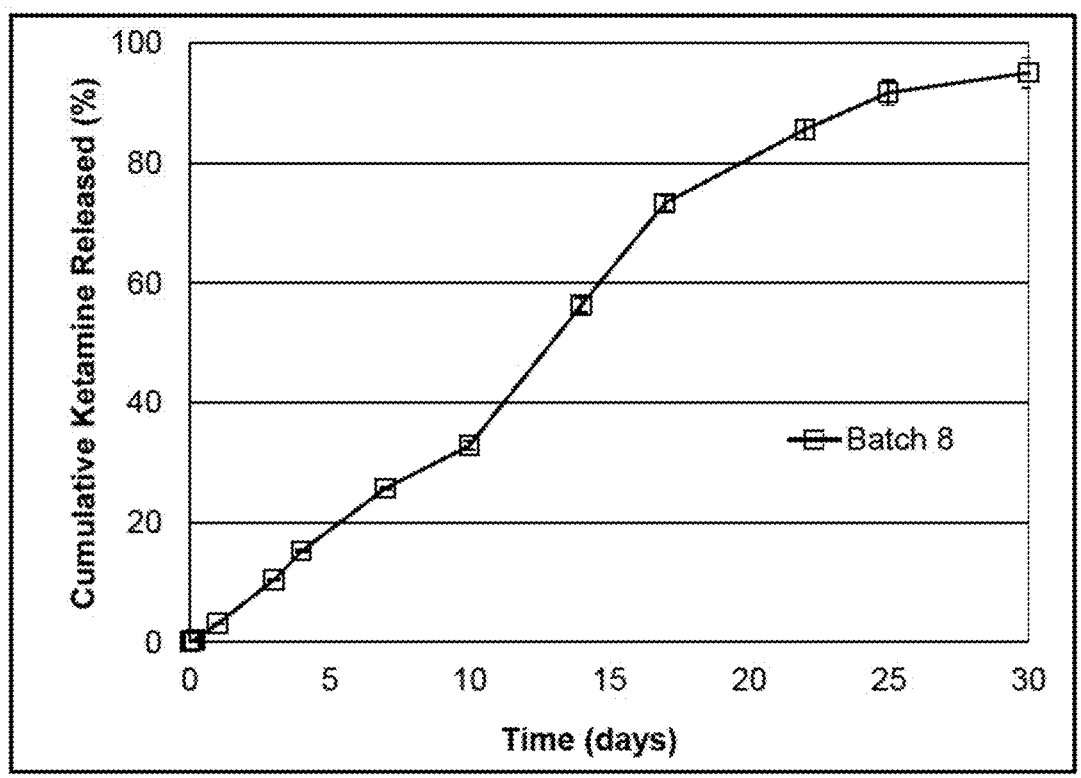
FIG. 7 is a graph showing an amount of ketamine released in vitro over time from an example double emulsified microsphere formulation.

Batch No. 8 was tested in an in vitro assay mimicking physiological conditions. The cumulative percent release of ketamine overtime is shown graphically in FIG. 5 (in comparison to other single and double emulsified batches, as a function of the inherent viscosity of the biodegradable polymer) and in FIG. 7.

Example 10—Preparation and Evaluation of a Low Inherent Viscosity (0.66 dL/g) PLA-Based Double Emulsion Microsphere Formulation, Comprising PVA in the IA Component Batch No. 9: The organic component was formed by dissolving 70.0 g of an ester end-capped PLA Ashland Viatel 07 E polymer (IV=0.66 dL/g) in 388 g of DCM and 46 g of ethanol (5:1 ratio, by volume), followed by the addition of esketamine (30.0 g) with mixing until completely dissolved. The organic component was homogenized with an IA component consisting of 11 mL of a 0.35% PVA solution in a T25 Ultra-turrax high-speed homogenizer operating at 21,500 rpm for 45 seconds to form the PE.

The PE was pumped into a Levitronix i100 (as described in US20210001290) operating at 1,600 rpm at a rate of 30 mL/minute, along with the CP comprising water and 0.35% PVA, which was pumped at a rate of 2 L/min, for a CP:PE ratio of 66:1.

The formed or forming microspheres exited the homogenizer and entered an SRV. Deionized water was added to the SRV at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to obtain a free-flowing powder with a yield of about 72%. The drug load was 14.6 wt/wt % (49% drug encapsulation efficiency based on a target drug load of 30 wt/wt %). The average particle size was 38 μm ($D_{10}$), 75 μm ($D_{50}$), 123 μm ($D_{90}$).

Batch No. 9 was tested in an in vitro assay mimicking physiological conditions. The cumulative percent release of ketamine overtime is shown graphically in FIG. 5 (in comparison to other single and double emulsified batches, as a function of the inherent viscosity of the biodegradable polymer).

Example 11—Preparation and Evaluation of a Higher Inherent Viscosity (1.80 dL/g) PLA-Based Double Emulsion Microsphere Formulation Batch No. 10: The organic component was formed by dissolving 7.0 g of an ester end-capped PLA Evonik LG 207S polymer (IV=1.80 dL/g) in 63 g of DCM and 4.6 g of ethanol (8:1 ratio, by volume), followed by the addition of esketamine (3.0 g) with mixing until completely dissolved. The organic component was homogenized with an IA component consisting of 1 mL of a 0.35% PVA solution in a T25 Ultra-turrax high-speed homogenizer operating at 21,500 rpm for 30 seconds to form the PE.

The PE was pumped into a Levitronix i100 (as described in US20210001290) operating at 1,600 rpm at a rate of 30 mL/minute, along with the CP comprising water and 0.35% PVA, which was pumped at a rate of 2 L/min, for a CP:DP ratio of 66:1.

The formed or forming microspheres exited the homogenizer and entered an SRV. Deionized water was added to the SRV at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to obtain a free-flowing powder with a yield of about 56%. The drug load was 17.4 wt/wt % (58% drug encapsulation efficiency based on a target drug load of 30 wt/wt %). The average particle size was 27 μm ($D_{10}$), 67 μm ($D_{50}$), 136 μm ($D_{90}$).

Batch No. 10 was tested in an in vitro assay mimicking physiological conditions. The cumulative percent release of ketamine overtime is shown graphically in FIG. 5 (in comparison to other single and double emulsified batches, as a function of the inherent viscosity of the biodegradable polymer).

Example 12—Pharmacokinetics Study in Rats of Batch Nos. 7, 9, and 10

The pharmacokinetic profile of ketamine following a subcutaneously injected dose of time-released ketamine formulation in male Sprague-Dawly rats was studied. The rats received a 50 mg/kg dose of the indicated Batch No., having a ketamine concentration of 33.33 mg/mL and a volume of 1.5 mL/kg. Microsphere suspension concentrations (mg/mL) were as follows: (a) Batch No. 7: 130.21; (b) Batch No. 9: 228.31; and (c) Batch No. 10: 191.57. Blood was collected at 0.5, 1, 2, 4, 24, 48, 168, 264, 360, 480, 600, 720, 840, 960, 1080, and 1200 hours. FIG. 8 is a graph showing the measured mean blood concentration (ng/mL) of ketamine as a function of time for Batches Nos. 7 (Example 7), 9 (Example 10), and 10 (Example 11).

Example 13—Low Inherent Viscosity (0.67 dL/g) PLA-Based Double Emulsion Microsphere Formulations, with a CP:PE Ratio of 100:1

Batch Nos. 11A and 11B: An organic component was formed by dissolving 14.0 g of an ester end-capped PLA Ashland DL Viatel 07 E polymer (IV=0.67 dL/g) in 77.58 g of DCM and 9.2 g of ethanol (5:1 ratio, by volume), followed by the addition of esketamine (6.0 g) with mixing until completely dissolved. The organic component was homogenized with an IA component consisting of 2.18 g of 0.35% PVA solution in a T25 Ultra-turrax high-speed homogenizer operating at 21,500 rpm for 30 seconds to form the PE having an organic:IA component ratio of about 49:1 (on a mass basis).

The primary emulsion was pumped into a Levitronix i100 (as described in US20210001290) operating at 1,600 rpm at a rate of 20 mL/minute, along with a CP comprising water and 0.35% PVA, which was pumped at a rate of 2 L/min, for a CP:PE ratio of 100:1.

The formed or forming microspheres exited the homogenizer and a portion (Batch No. 11A) of the suspension entered a first SRV, wherein the microspheres were subjected immediately to deionized water at 2 L/min. Solvent removal was achieved by washing the microspheres with ambient water (i.e., 25° C.) and hot water (35-39° C.) and filtering them through a hollow fiber filter. The bulk suspension was collected via filtration and lyophilized to yield 6.6 g of a free-flowing powder. The drug load was 23.0 wt/wt % (77% drug encapsulation efficiency based on a target drug load of 30 wt/wt %). The average particle size was 53 µm ($D_{10}$), 94 µm ($D_{50}$), 152 m ($D_{90}$).

A second portion of the suspension (Batch No. 11B) entered a second SRV, wherein it was held for four hours. At the conclusion of the four hour hold, the microspheres were washed, filtered, and lyophilized as described with respect to Batch No. 11A to yield 6.7 g of a free-flowing powder. The drug load was 9.2 wt/wt % (31% drug encapsulation efficiency based on a target drug load of 30 wt/wt %). The mean particle size was 50 µm ($D_{10}$), 90 µm ($D_{50}$), 143 µm ($D_{90}$). The total yield of Batch Nos. 11A and 11B was 66.3%.

Figure 9:
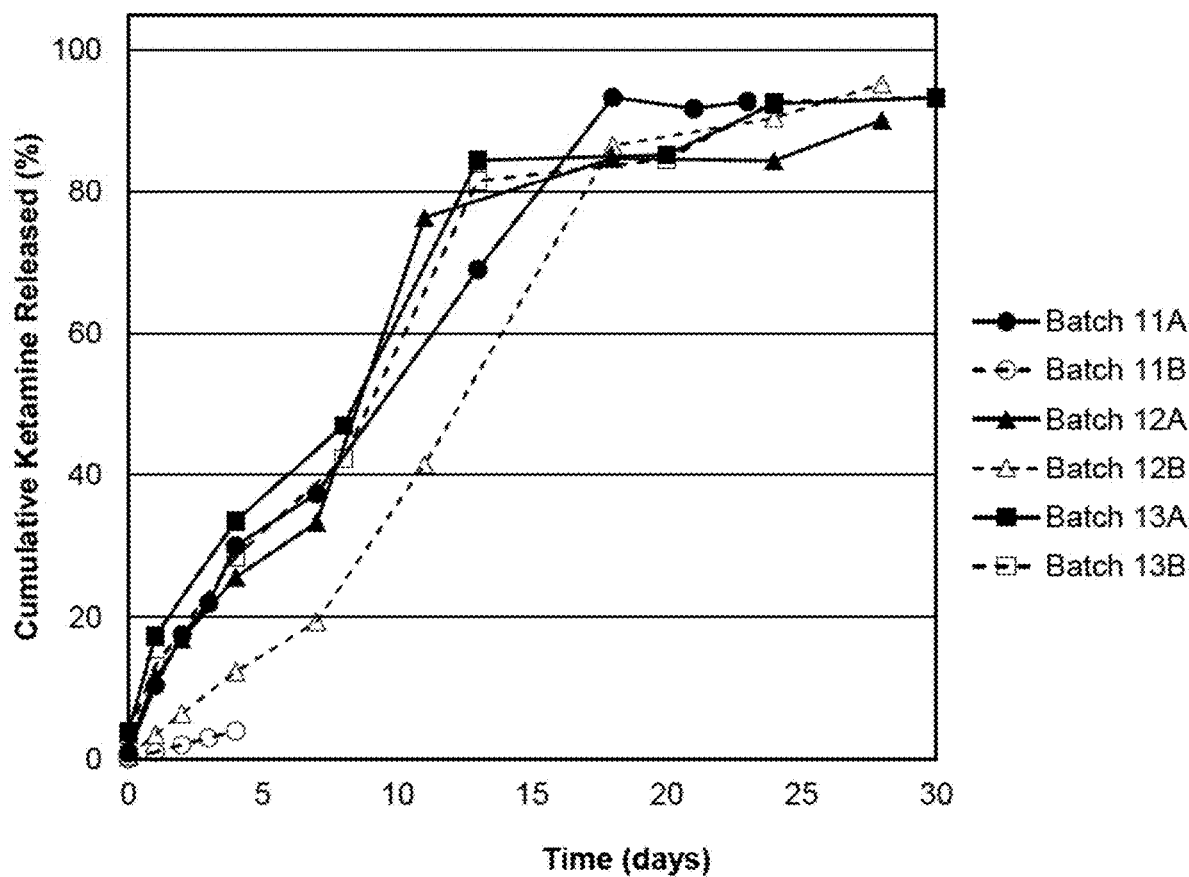
FIG. 9 is a graph showing an amount of ketamine release in vitro over time from several microsphere formulations prepared using a double emulsification technique.

Batch Nos. 11A and 11B were tested in an in vitro assay mimicking physiological conditions. The cumulative percent release of ketamine over time is shown graphically in FIG. 9.

Example 14—Low Inherent Viscosity (0.67 dL/g) PLA-Based Double Emulsion Microsphere Formulations, with a CP:PE Ratio of 80:1

Batch Nos. 12A and 12B: An organic component was formed by dissolving 10.5 g of an ester end-capped PLA Ashland DL 07 E polymer (IV=0.67 dL/g) in 58.19 g of DCM and 6.9 g of ethanol (5:1 ratio, by volume), followed by the addition of esketamine (4.5 g) with mixing until completely dissolved. The organic component was homogenized with an IA component consisting of 1.64 g of 0.35% PVA solution in a T25 Ultra-turrax high-speed homogenizer operating at 21,500 rpm for 30 seconds to form the PE having an organic:IA component ratio of about 49:1 (on a mass basis).

The PE was pumped into a Levitronix i100 (as described in US20210001290) operating at 1,600 rpm at a rate of 25 mL/minute, along with a CP comprising water and 0.35% PVA, which was pumped at a rate of 2 L/min, for a CP:PE ratio of 80:1.

The formed or forming microspheres exited the homogenizer and a portion (Batch No. 12A) of the suspension entered a first SRV, wherein the microspheres were subjected immediately to deionized water at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to yield 0.89 g of a free-flowing powder. The drug load was 24.8 wt/wt % (83% drug encapsulation efficiency based on a target drug load of 30 wt/wt %). The mean particle size was 57 µm ($D_{10}$), 111 µm ($D_{50}$), 189 µm ($D_{90}$).

A second portion (Batch No. 12B) of the suspension entered a second SRV, wherein it was held for four hours. At the conclusion of the four hour hold, the microspheres were washed, filtered, and lyophilized as described with respect to Batch No. 12A to yield 7.2 g of a free-flowing powder. The drug load was 17.4 wt/wt % (58% drug encapsulation efficiency based on a target drug load of 30 wt/wt %). The mean particle size was 54 µm ($D_{10}$), 99 µm ($D_{50}$), 161 µm ($D_{90}$). The total yield of Batch Nos. 12A and 12B was 54%.

Batch Nos. 12A and 12B were tested in an in vitro assay mimicking physiological conditions. The cumulative percent release of ketamine over time is shown graphically in FIG. 9.

Example 15—Low Inherent Viscosity (0.67 dL/g) PLA-Based Double Emulsion Microsphere Formulations, with a CP:PE Ratio of 80:1

Batch Nos. 13A and 13B: An organic component was formed by dissolving 10.5 g of an ester end-capped PLA Ashland DL 07 E polymer (IV=0.67 dL/g) in 58.19 g of DCM and 6.9 g of ethanol (5:1 ratio, by volume), followed by the addition of esketamine (4.5 g) with mixing until completely dissolved. The organic component was homogenized with an IA component consisting of 1.64 g of 0.35% PVA solution in a T25 Ultra-turrax high-speed homogenizer operating at 21,500 rpm for 30 seconds to form the PE having an organic:IA component ratio of about 49:1 (on a mass basis).

The PE was pumped into a Levitronix i100 (as described in US20210001290) operating at 1,600 rpm at a rate of 25 mL/minute, along with a CP comprising water and 0.35% PVA, which was pumped at a rate of 2 L/min, for a CP:DP ratio of 80:1.

The formed or forming microspheres exited the homogenizer and a portion (Batch No. 13A) of the suspension entered a first SRV, wherein the microspheres were subjected immediately to deionized water at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to yield 2.99 g of a free-flowing powder. The drug load was 29.4 wt/wt % (98% drug encapsulation efficiency based on a target drug load of 30 wt/wt %). The mean particle size was 46 μm ($D_{10}$), 104 μm ($D_{50}$), 190 μm ($D_{90}$).

A second portion (Batch No. 13B) of the suspension entered a second SRV, wherein it was held for four hours. At the conclusion of the four hour hold, the microspheres were washed, filtered, and lyophilized as described with respect to Batch No. 13A to yield 7.09 g of a free-flowing powder. The drug load was 26.4 wt/wt % (88% drug encapsulation efficiency based on a target drug load of 30 wt/wt %). The mean particle size was 52 μm ($D_{10}$), 99 μm ($D_{50}$), 162 m ($D_{90}$). The total yield of Batch Nos. 13A and 13B was 67%.

Batch Nos. 13A and 13B were tested in an in vitro assay mimicking physiological conditions. The cumulative percent release of ketamine over time is shown graphically in FIG. 9.

Example 16—Low Inherent Viscosity (0.67 dL/g) PLA-Based Double Emulsion Microsphere Formulations, with CP (1.0% PVA) and a CP:PE Ratio of 80:1

Batch Nos. 14A and 14B: An organic component was formed by dissolving 12.45 g of an ester end-capped PLA Ashland DL 07 E polymer (IV=0.67 dL/g) in 70.74 g of DCM and 8.39 g of ethanol (5:1 ratio, by volume), followed by the addition of esketamine (2.55 g) with mixing until completely dissolved. The organic component was homogenized with an IA component consisting of 1.64 g of 0.35% PVA solution in a T25 Ultra-turrax high-speed homogenizer operating at 21,500 rpm for 30 seconds to form the PE having an organic:IA component ratio of about 57:1 (on a mass basis).

The PE was pumped into a Levitronix i100 (as described in US20210001290) operating at 1,600 rpm at a rate of 25 mL/minute, along with a CP comprising water and 1.0% PVA, which was pumped at a rate of 2 L/min, for a CP:PE ratio of 80:1.

The formed or forming microspheres exited the homogenizer and a portion (Batch No. 14A) of the suspension entered a first SRV, wherein the microspheres were subjected immediately to deionized water at 2 L/min. Solvent removal was achieved by washing the microspheres with ambient water (i.e., 25° C.) and hot water (35-39° C.) and filtering them through a hollow fiber filter.

The bulk suspension was collected via filtration and lyophilized to yield 2.99 g of a free-flowing powder. The drug load was 14.5 wt/wt % (85% drug encapsulation efficiency based on a target drug load of 17 wt/wt %). The mean particle size was 32 μm ($D_{10}$), 87 μm ($D_{50}$), 149 μm ($D_{90}$).

A second portion (Batch No. 14B) of the suspension entered a second SRV, wherein it was held for four hours. At the conclusion of the four hour hold, the microspheres were washed, filtered, and lyophilized as described with respect to Batch No. 14A to yield 6.95 g of a free-flowing powder. The drug load was 13.7 wt/wt % (81% drug encapsulation efficiency based on a target drug load of 17 wt/wt %). The mean particle size was 37 μm ($D_{10}$), 88 μm ($D_{50}$), 148 μm ($D_{90}$). The total yield of Batch Nos. 14A and 14B was 75%.

Figure 10:
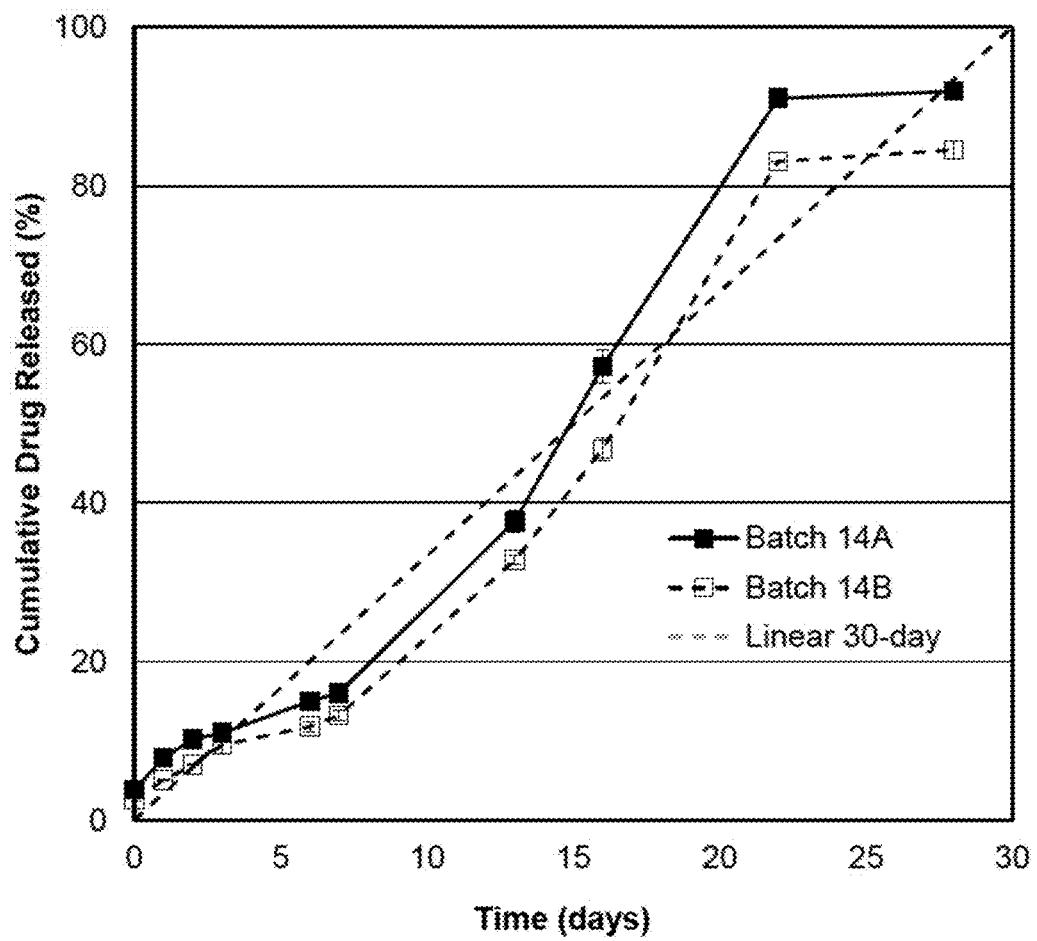
FIG. 10 is a graph showing an amount of ketamine release in vitro over time versus a linear 30 day release from a microsphere formulation prepared using a double emulsification technique.

Batch Nos. 14A and 14B were tested in an in vitro assay mimicking physiological conditions. The cumulative percent release of ketamine over time is shown graphically in FIG. 10 compared to an ideal 30 day release profile.

The aspects disclosed herein are not intended to be exhaustive or to be limiting. A skilled artisan would acknowledge that other aspects or modifications to instant aspects can be made without departing from the spirit or scope of the invention. The aspects of the present disclosure, as generally described herein and illustrated in the figures, can be arranged, substituted, combined, separated, and designed in a wide variety of different configurations, all of which are contemplated herein.

Unless otherwise specified, "a," "an," "the," "one or more of," and "at least one" are used interchangeably. The singular forms "a", "an," and "the" are inclusive of their plural forms. The recitations of numerical ranges by endpoints include all numbers subsumed within that range (e.g., 1 to 5 includes 1, 1.5, 2, 2.75, 3, 3.80, 4, 5, etc.). The terms "comprising" and "including" are intended to be equivalent and open-ended. The phrase "consisting essentially of" means that the composition or method may include additional ingredients and/or steps, but only if the additional ingredients and/or steps do not materially alter the basic and novel characteristics of the claimed composition or method. The phrase "selected from the group consisting of" is meant to include mixtures of the listed group.

When reference is made to the term "each," it is not meant to mean "each and every, without exception." For example, if reference is made to microsphere formulation comprising polymer microspheres, and "each polymer microsphere" is said to have a particular ketamine content, if there are 10 polymer microspheres, and two or more of the polymer microspheres have the particular ketamine content, then that subset of two or more polymer microspheres is intended to meet the limitation.

The term "about" in conjunction with a number is intended to include ±10% of the number. This is true whether "about" is modifying a stand-alone number or modifying a number at either or both ends of a range of numbers. In other words, "about 10" means from 9 to 11. Likewise, "about 10 to about 20" contemplates 9 to 22 and 11 to 18. In the absence of the term "about," the exact number is intended. In other words, "10" means 10.

What is claimed is:

1. A microsphere formulation, comprising:
   polymer microspheres, each polymer microsphere comprising:
   esketamine in a concentration of about 10 wt/wt % to about 30 wt/wt %; and
   a biodegradable poly(lactide) polymer in a concentration of about 70 wt/wt % to about 90 wt/wt %, wherein the biodegradable poly(lactide) polymer has an inherent viscosity from about 0.6 dL/g to about 0.7 dL/g;
   wherein the polymer microspheres have a particle size greater than 60 μm ($D_{50}$);
   wherein the polymer microspheres are characterized in that each of the polymer microspheres comprises an internal polymer phase, a plurality of internal macrovoids dispersed within the internal polymer phase, and an outer surface substantially free of voids; and
   wherein the polymer microspheres are prepared by a method that does not include the use of a porogen, the method comprising:

(i) contacting the esketamine with the biodegradable poly(lactide) polymer in the presence of a solvent to form an organic component;
(ii) emulsifying an inner aqueous component comprising water with the organic component to form a primary emulsion;
(iii) emulsifying the primary emulsion with a continuous phase comprising water to form a secondary emulsion;
(iv) removing the solvent from the secondary emulsion to form the polymer microspheres; and
(v) subjecting the polymer microspheres to dehydration.

2. The microsphere formulation of claim 1, wherein the polymer microspheres have a particle size of about 70 μm ($D_{50}$) to about 110 μm ($D_{50}$).

3. The microsphere formulation of claim 1, wherein each polymer microsphere has an esketamine concentration of between about 12 wt/wt % to about 17 wt/wt % and a biodegradable poly(lactide) polymer concentration of about 83 wt/wt % to about 88 wt/wt %.

4. The microsphere formulation of claim 1, characterized in that about 75% to 100% of the esketamine is released over a period of between about 25 to about 35 days of injection into a human subject, but not more than about 10% of the esketamine has been released within 24 hours of injection into the human subject.

5. A pharmaceutical composition comprising the microsphere formulation of claim 1.

6. The microsphere formulation of claim 1, wherein each of the polymer microspheres is further characterized in that the esketamine is dispersed within the internal polymer phase.

* * * * *